United States Patent [19]
Hardy et al.

[11] 4,050,895
[45] Sept. 27, 1977

[54] OPTICAL ANALYTICAL DEVICE, WAVEGUIDE AND METHOD

[75] Inventors: Edgar E. Hardy, Kettering; Donald J. David, Centerville, both of Ohio

[73] Assignee: Monsanto Research Corporation, St. Louis, Mo.

[21] Appl. No.: 724,035

[22] Filed: Sept. 17, 1976

Related U.S. Application Data

[63] Continuation-in-part of Ser. No. 617,120, Sept. 26, 1975, abandoned, which is a continuation-in-part of Ser. No. 522,558, Nov. 11, 1974, abandoned.

[51] Int. Cl.² ............... G01N 21/22; G01N 33/16
[52] U.S. Cl. ............... 23/230 R; 23/230 B; 23/253 R; 250/227; 252/408; 350/96 R; 356/209; 428/392; 424/12
[58] Field of Search ............ 23/230 R, 230 B, 253 R; 350/96 R; 428/392

[56] References Cited

U.S. PATENT DOCUMENTS

| | | | |
|---|---|---|---|
| 2,666,355 | 1/1954 | Trurnit | 23/230 R X |
| 3,282,149 | 11/1966 | Shaw | 250/227 X |
| 3,431,411 | 3/1969 | Harrick | 350/96 R |
| 3,513,319 | 5/1970 | Broerman | 250/227 X |
| 3,647,406 | 3/1972 | Fisher | 350/178 X |
| 3,770,380 | 11/1973 | Smith | 424/12 |
| 3,904,373 | 9/1975 | Harper | 23/253 TP |

*Primary Examiner*—Sidney Marantz
*Attorney, Agent, or Firm*—Bruce Stevens

[57] ABSTRACT

A device for detecting a first material comprising (a) a waveguide having on a peripheral surface of the waveguide a second material which on contacting the first material selectively combines with the first material to measurably change the light transmitting capabilities of the waveguide, (b) a light source positioned to transmit light into the waveguide, and (c) means for measuring the light exiting from the waveguide. The waveguide described in the previous sentence is a new article of manufacture. The device is useful in a method for detecting a first material comprising the steps of (a) exposing a waveguide having on a peripheral surface of the waveguide a second material to an unknown material which may contain the first material, and second material upon being contacted by the first material selectively combines with the first material to measurably change the light transmitting capabilities of the waveguide; (b) transmitting light through the waveguide after exposure in step (a); and, (c) detecting the light transmitted in step (b) as a measure of the first material. The device and method can be used in either qualitative or quantitative analysis.

34 Claims, 5 Drawing Figures

OPTICAL ANALYTICAL DEVICE, WAVEGUIDE AND METHOD

CROSS-REFERENCE TO RELATED APPLICATIONS

This application is a continuation-in-part of application Ser. No. 617,120, filed Sept. 26, 1975, now abandoned, which is a continuation-in-part of application Ser. No. 522,558, filed Nov. 11, 1974, now abandoned. A related application is Ser. No. 689,403, filed May 24, 1976, for Waveguide Holder-Humidifier.

Another related application is Ser. No. 705,962, filed July 16, 1976.

BACKGROUND OF THE INVENTION

1. Field of the Invention

The invention relates to an optical analytical method and device and to a waveguide or optical fiber useful in the device.

2. Description of the Prior Art

U.S. Pat. No. 2,964,993 describes an apparatus for measuring fluids by analyzing the specific gravity or composition comprising a longitudinally extending radiant energy guide which is of a transparent radiant energy transmitting material such as sapphire, quartz or Pyrex.

U.S. Pat. No. 2,977,842 describes an apparatus and method for measuring the quantity of moisture in a moving sheet such as paper using fiber optics.

U.S. Pat. No. 3,071,038 describes a radiant energy measuring apparatus having a radiant energy transmitting light guide for obtaining a continuous accurate measurement of changes taking place in density and/or specific gravity of composition of a fluid that is flowing over the peripheral surface of this guide.

U.S. Pat. No. 3,370,502 describes an absorption cell means having a rod with a cell surrounding the rod, radiant energy being directed at one end of the rod means and passing down the rod with multiple internal reflection.

U.S. Pat. No. 3,409,404 teaches the optical properties of a cholesteric liquid crystalline material are changed when the cholesteric material is contacted with another material. A variety of materials, particularly vapors, are identified by observing their effect on cholesteric liquid crystalline materials. The most convenient observable effect is a change in the color of the cholesteric material and, if necessary, comparing the change effected by a known standard material. An anayltical device may comprise one or more distinct elements of cholesteric liquid crystalline material. Suitable cholesteric liquid crystalline materials include a wide variety of compounds, and mixtures thereof, derived from the cholesterol.

U.S. Pat. No. 3,752,584 describes a spectroscopic device and method of using attenuated total reflection techniques for analysis of samples of particulate solids in a fluid. A beam of radiation is passed through an optical cell comprising a plurality of elongated, totally internally reflecting elements, e.g., fiber optics arranged as a mechanical filter. When fluid containing the particles is passed transversely across the cell, the latter are trapped in the filter whereupon radiation passing through the elements is selectively absorbed, thus providing an optical output having an absorption spectrum which may be utilized to identify the sample.

U.S. Pat. No. 3,805,066 describes a smoke detecting device utilizing optical fibers with smoke paths in a series arrangement interrupting the light path.

SUMMARY OF THE INVENTION

A device for detecting a first material comprising (a) a waveguide having on a peripheral surface of the waveguide a second material which on contacting the first material selectively combines with the first material to measurably change the light transmitting capabilities of the waveguide, (b) a light source positioned to transmit light into the waveguide, and (c) means for measuring the light exiting from the waveguide. The waveguide described in the previous sentence is a new article of manufacture. The device is useful in a method of detecting a first material comprising the steps of (a) exposing a waveguide having on a peripheral surface of the waveguide a second material to an unknown material which may contain the first material, the second material upon being contacted by the first material selectively combines with the first material to measurably change the light transmitting capabilities of the waveguide; (b) transmitting light through the waveguide after exposure in step (a); and, (c) detecting the light transmitted in step (b) as a measure of the first material. The device and method can be used in either qualitative or quantitative analysis.

The waveguide can be coated with, impregnated with or in some instances can be made from the second material provided the second material will adequately transmit light, and in some instance the second material may constitute reactive groups attached to the waveguide. The first material can be selectively combined with the second material by adsorption or absorption, chemically including biochemically reacting with and/or complexing with the second material. The waveguide coating preferably conforms to FIGS. 1B, i.e. both where $n_o < n_1$ and $n_o \approx n_1$, providing for multiple internal reflections through the second material, e.g. the coating.

In the case of a coated waveguide, the waveguide might be either solid or hollow, e.g. a hollow or solid cylinder, and in the case of a hollow cylinder the coating could be on the inner or outer surfaces or both, but normally the ends of the solid rods will not be coated rather only the longitudinal circumferential (peripherial) area, i.e. not the light inlet and exit ends of the waveguide, except in some cases where it may be desirable to pass the light through a coating on the ends to absorb certain wavelength light. Obviously, in quantitative detection, the amount of the second material on the waveguide needs to be in excess of that needed to combine with the anticipated maximum amount of the first material to be detected, and preferably the second material is in substantial excess.

Waveguides can be made from transparent material such as sapphire, glass, Pyrex or other transparent inorganic material; or from transparent plastics such as polystyrene, poly-α-methylstyrene, polymethylmethacrylate or other transparent plastic material. The waveguides can be of any convenient shape and size but for greatest sensitivity will normally be elongated in the direction of the flow of light. Cylindrical waveguides, sometimes called optical fibers, will normally be used; however, square, rectangular, oval or other cross-section fibers or rods can be used.

The light source can be a commercially available light source being a substantially white light source or can be colored or substantially monochromatic in the infrared, ultraviolet, yellow, orange, green, blue or other color ranges; however, as the discussion of FIG. 4 indicates filters can be used to obtain colored light. Monochromatic light in various colors can be supplied by light emitting diode (LED's). Laser light, especially dye laser light, can also be used, if desired. As is indicated in this discussion of FIG. 4, a particular color such as green in that case can be the most desirable depending on the color or compensation of the coating developed on the waveguide.

DESCRIPTION OF THE PREFERRED EMBODIMENTS

The waveguide-coated combination, which acts as a specific collector/sensor, can be chosen to provide a coating whose refractive index is either higher, the same, or lower than that of the waveguide. Usually, it is preferred that the coating be either a water-soluble or non-water-soluble polymer with a reactant in it depending upon its compatibility with the desired reactants; however, in some instances the coating will be only a reactant. The lower refractive index condition is that normally employed in optical guide applications and results in the mechanism illustrated in FIG. 1A.

Figure 1:
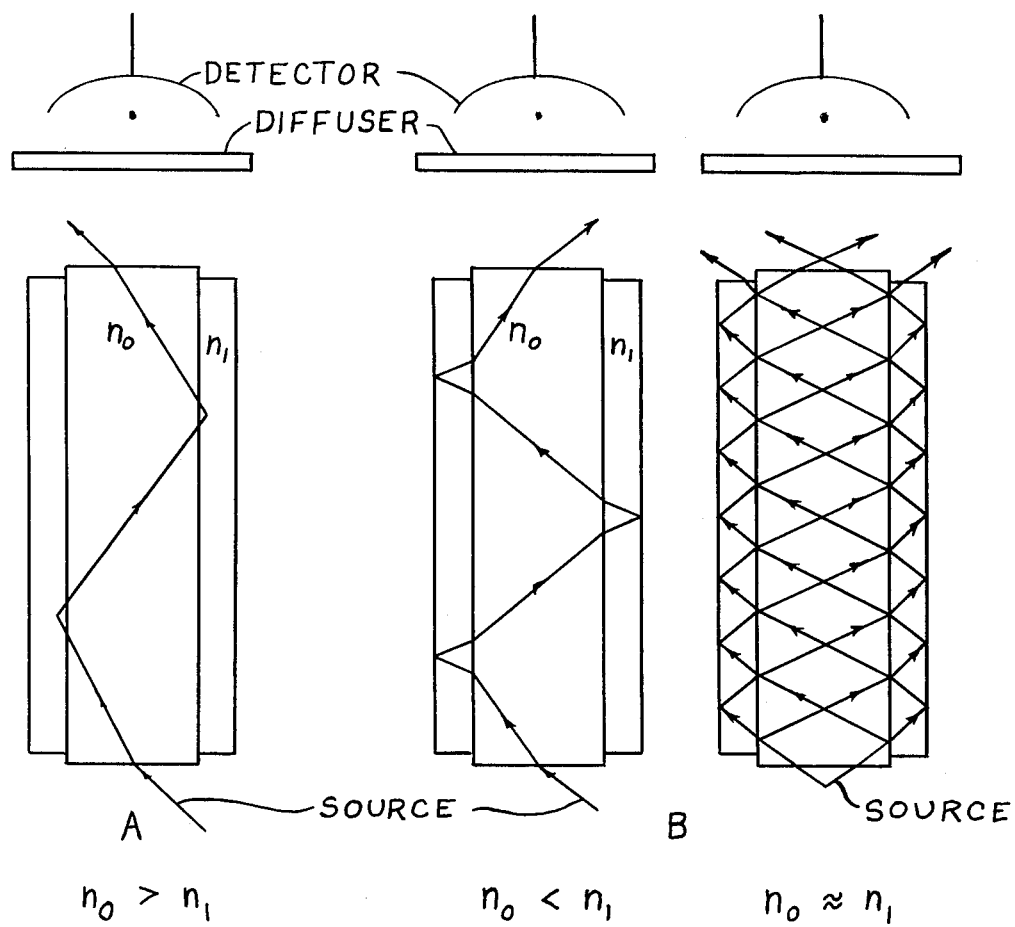
FIG. 1 shows schematic models of light transmitting mechanisms of waveguides of the invention.

Employing a coating with refractive index higher than or approximately equal to that of the waveguide, the mechanisms shown in FIG. 1B would be operative. Although either approach can be used, Model 1A would result in lower sensitivity, since the evanescent wave interactions occur only in the region of the rod-coating interface. In either of the mechanisms of Model 1B, essentially all radiation is transmitted through the entire coating and in this way allows solid state spectrophotometric measurements to be made in situ.

Figure 2:
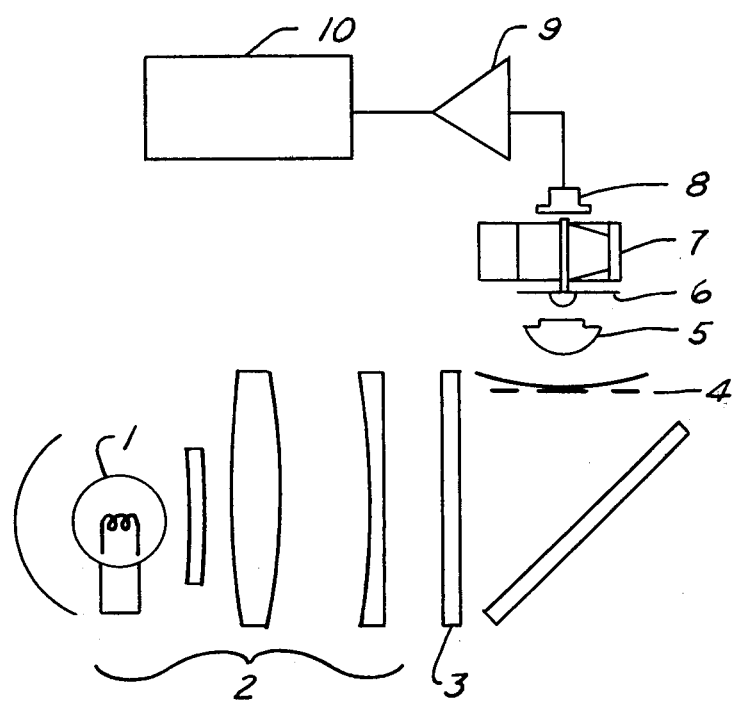
FIG. 2 is a block diagram of a device of the invention.

In order to measure the light transmittance, an instrument or device was designed and constructed to provide quantitative analytical measurements. This particular device accommodates glass rods 0.9 mm to 1.3 mm in diameter and either 10 mm or 20 mm long. A schematic diagram showing the basic components is presented in FIG. 2. The components are:

1. A tungsten filament lamp light source.
2. A condenser system to produce nearly collimated light.
3. A filter for wavelength selection.
4. An annular aperature to block axial light rays.
5. A condenser to produce a hollow cone of light rays.
6. Coupling hemispheres and aperatures to couple large angle rays into the rod.
7. A rod mount to accurately position rods with respect to the aperature while presenting a minimum of surface contact.
8. A silicon photodiode detector.
9. An operational amplifier operating as "current-to-voltage" converter.
10. A 3½ digit digital voltmeter for relative transmittance readout.

Figure 3:
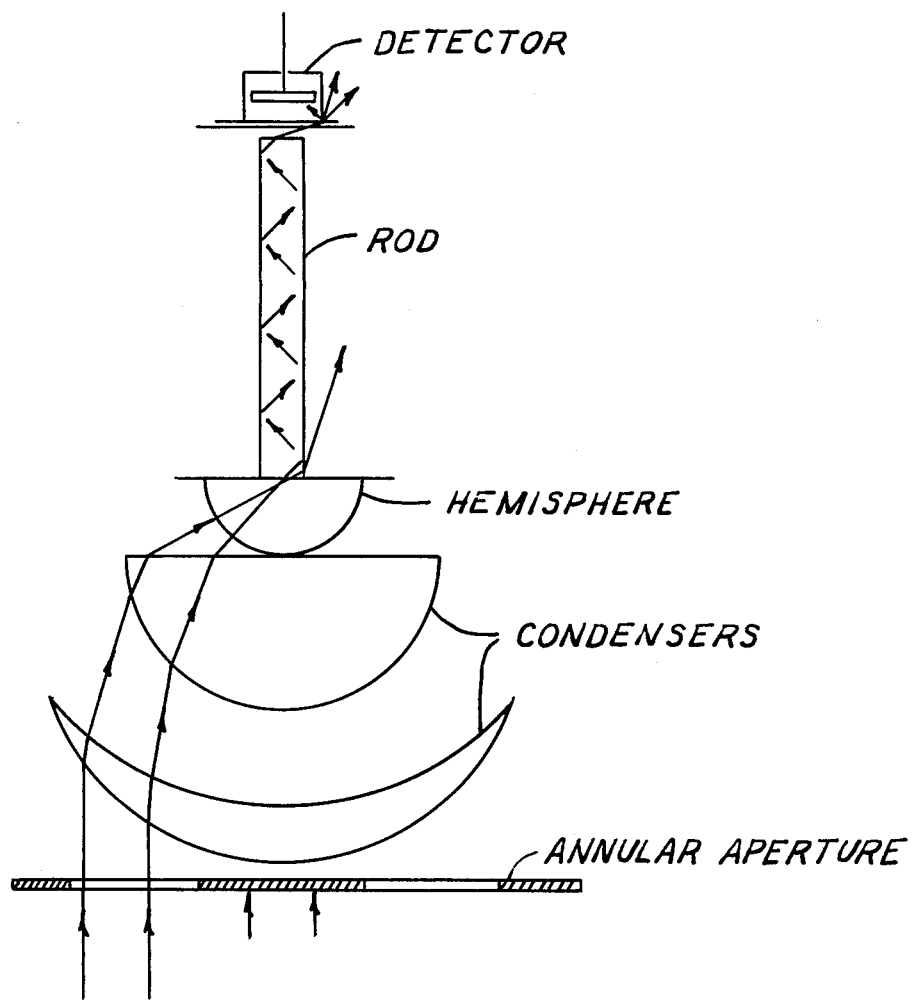
FIG. 3 is a schematic detailed view of the optics of the invention.

A schematic optical diagram is shown in FIG. 3, with rod dimensions exaggerated to show basic instrumental operation. The light from the tungsten lamp is collimated using both mirror and lens condensers. The light then passes through a heat absorbing glass filter and a variable color selection filter. A front surface mirror deflects the light 90° in the vertical direction. An annular aperature blocks axial light rays and defines the range of cone angles for light rays propagating in the quartz rods. The substage condenser converts the collimated beam into a strongly converging hollow cone of light. The hemispherical lens and circular aperture couple the light into the rod.

After multiple reflections within the rod, the light emerges at the upper face and is scattered by a diffuser, part of the light going into the silicon photodiode detector. The photodiode is operated in photovoltaic mode, the operational amplifier acting as a current sink to minimize the voltage across the diode. The amplifier output is a low impedance voltage proportional to the input current over a range of $10^{-11}$ ampere to $10^{-3}$ ampere. An output voltage suitable for the 200 mV full-scale digital panel meter is selected by a decade range switch.

In use, the amount of light transmitted through the rod after coating but before exposure is first recorded with the device. When the coating is exposed to a material of analytical interest, the ensuing reaction changes the coating, and the transmission of light through the waveguide changes in proportion to the concentration of the reactant species. Depending on the particular application it may be desirable that the coated waveguides be exposed to the material being detected either positioned in the device for measuring light transmission or the coated waveguides may be exposed separate from the device and then positioned in the device for light transmission measurements. The phenomenon is controlled by the well-known waveguide theories that have been described by Kapany*.

*Kapany, N.S., "Fiber Optics," Academic Press, New York, 1967.

The composition of a coating that has been applied to a waveguide can be changed by the following mechanisms which lead to detection by the device through sensing a change in refractive index and/or by absorption, adsorption or scattering processes:

1. Chemical reaction of a component with the active ingredient (reactant) in the coating of the waveguide to produce a product which is essentially the same color as the starting material.

The device senses this change due to a change in the refractive index of the product material. This approach has the disadvantage that the end product is not colored and therefore not wavelength selective. As a consequence moisture is sensed and interferes but this may be eliminated by drying the coated waveguide to the same degree as when the test was initiated. The product can be quite stable depending upon the specific reaction chosen.

The essential factor is that the critical angle beyond which entering the light rays are no longer transmitted through the rod is given by $\sin \theta c = (n_1/n_o)$, wherein $n_o$, the refractive index of the core, is greater than $n_1$, the refractive index of the coating. Thus, the coated waveguide acts as a sensitive light amplifier whose electrical analog is that of a vacuum tube or transistor-operated amplifier in that a small change on the outer surface of the rod controls a large change in the light transmitted through the rod.

2. Chemical reaction of a component with the active reactant in the coated waveguide to produce a stable product which is clear and colored.

This approach offers specificity because of the wavelength selection capabilities of the device, and therefore achromatic light can be used to compensate for moisture which contributes to the readings. The product can be quite stable depending upon the specific reaction chosen.

3. Chemical reaction of a component with the active reactant in the coated waveguide to produce a colored and/or non-colored precipitate.

In this instance whether or not the precipitate has color would make little difference since the light impinging on the particles would be mainly lost due to scattering. Moisture would interfere here but could be negated by drying to the same extent as when the test was initiated. The product can be quite stable depending upon the specific reaction chosen.

4. Complexation reaction of a component of interest with the active reactant in the coated waveguide to produce a colored and/or non-colored product.

In most cases the product will be colored. The product stability will generally not be as acceptable as that formed in a chemical reaction but will vary depending upon the specific reaction chosen.

5. An acid-base reaction of an acidic or basic component of interest with a pH-sensitive reactant in the coating to produce a colored reaction product.

This reaction is non-specific since any acidic or basic material will provide the same colored product. An advantage is that in this instance the reaction can be reversible and tailored to change at a desired concentration of component by proper selection of the initial pH and buffering agents present.

6. Use of physical processes such as absorption and/or adsorption of a component of interest by the reactant incorporated into the coating which has selective affinity for the component.

This approach may not hold the component strongly enough to provide the desired product stability.

We have found that moisture in the coating is necessary for many chemical and complexation reactions to occur. This is normally not a problem due to the moisture present in the air and the tendency of the coated collector/sensors to retain a relatively fixed amount of moisture; however, a preferred solution for moisture sensitive reactions is described in copending application Ser. No. 689,403, filed May 24, 1976, for a Waveguide Holder-Humidifier, and the teachings of the Waveguide Holder-Humidifier application are hereby incorporated by reference into this application.

EXAMPLE 1

This technique was tested by seeing if microgram quantities of sodium cyanide (NaCN) could be determined. A 1% aqueous solution of polyvinyl alcohol was prepared and 0.1% by weight of sodium picrate was added, which is known to respond to (CN-).* This solution was then used to uniformly coat the surface of the rods while the ends were protected.

*Feigl, Fritz, "Spot Tests in Inorganic Analysis," Elsevier Publishing Company, New York, 1958.

Light transmission of the dry, coated lightguides was measured before reaction. Known amounts of cyanide ion in the form of sodium cyanide were applied to the outer surface of the guides using a 5 ml Eppendorf pipette, the rods were dried, and transmission was again measured. The percent transmission based on the initial reading before exposure was then plotted as a function of (CN-) concentration.

Figure 4:
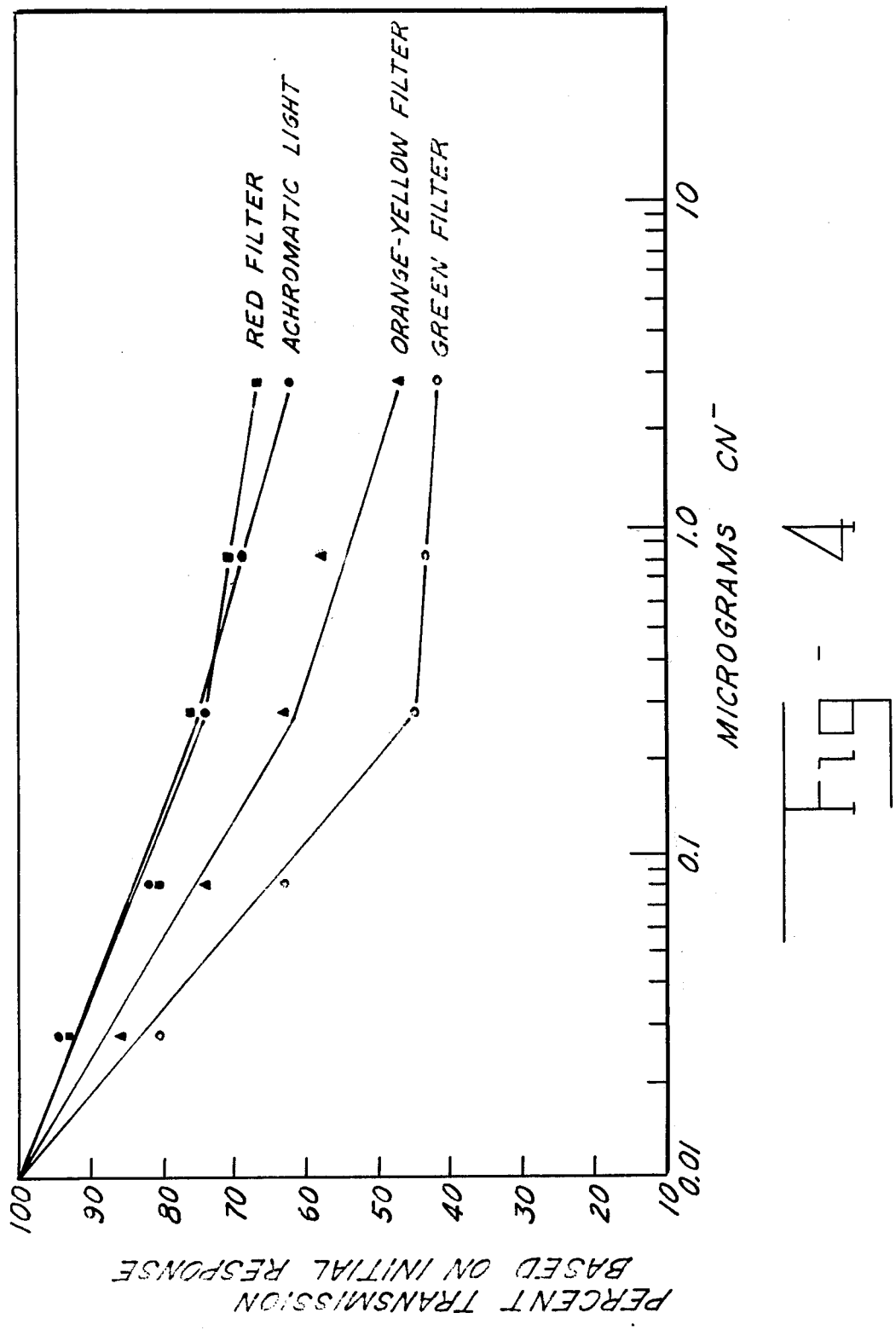
FIG. 4 is a graph of data obtained measuring $CN^-$ ion using a picrate coated waveguide of the invention; and, FIG. 5 is a graph of data obtained measuring hydrogen sulfide using a lead acetate in polyvinyl acetate coated waveguide of the invention.

The results shown in FIG. 4 were obtained. Reaction between the cyanide ion and the picrate changed the refractive index of the coating. The resulting change in light transmission through the guide was proportional to the concentration of the cyanide species. The multiple internal reflections enhanced the sensitivity, in that a small change in the optical characteristics of the coating caused a large change in the light transmitted through the system. It will be noted that the green filter provided the best sensitivity, which would be anticipated since green is the complementary color of the reddish-brown color of the reaction product. It is also noted that Beer's law is obeyed over the expected concentration range.

This technique was also successfully applied to the determination of gaseous HCN in air. The cyanide-in-air determination is not felt to be a typical of the applications that might be encountered and, therefore, it should be possible to apply this technique to a wide variety of components or pollutants of interest.

Initially, we anticipated problems both with the coatings themselves and with coating uniformity. While we did encounter problems along these lines, we have found that coatings can be applied uniformly once the coating procedures have been developed and that a number of different coating materials may be useful. In addition to water-soluble polyvinyl alcohol, Carbowax was found to perform quite well. Polymers that are not water-soluble will also be useful in some instances and sometimes the second material reactant without a polymer binder can be used to coat the waveguide, although in most instances a polymer binder will be preferred.

The most serious problem that we encountered, in the case of the determination of gaseous HCN, was the interference due to varying amounts of moisture in the air contributing to the reading obtained. We found that moisture absorption by the coated rods was proportional to the readings obtained at each of the wavelengths. However, since the reddish-brown reaction product was most sensitive to its complementary color or green, the green wavelength could be used to follow the reaction with sodium picrate while the moisture interference at this wavelength was corrected by using the change in the readings using achromatic light.

Thus, it is preferable to utilize a selective reaction which results in a colored product. The use of a selective reaction in which a non-color-selective end product is formed can still be utilized provided that the waveguide rods are dried to the same extent after the reaction as before.

EXAMPLE 2

This example describes the detecting of ammonia. The reaction between ammonia and ferric sulfate could take three possible routes:

Complexation (1)

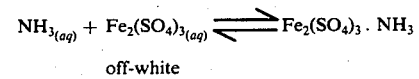

off-white

-continued

Lewis Acid-Base Reaction (2)

$$Fe_2(SO_4)_3 + 4H_2O \rightleftharpoons 2H_3O^+ + 2Fe(OH)^{+2} + 3SO_4^{-2}$$

$$NH_{3(aq)} + H_3O^+ \rightleftharpoons NH_4^+ + H_2O$$

Chemical Reaction (3)

$$2NH_{3(aq)} + 2Fe^{+3}_{(aq)} + 4(SO_4)^{-2}_{(aq)} + 2H^+_{(aq)} \rightleftharpoons Fe_2(SO_4)_3 \cdot (NH_4)_2SO_4$$

violet

The most desirable reaction is the chemical reaction to form the combined salt, ferric ammonium sulfate. Applying the basic thermodynamic considerations of $$aA + bB + \ldots \rightleftharpoons cC + dD$$

$$\Delta G^0 = cG_C^0 + dG_D^0 - aG_A^0 - bG_B^0$$

$$\Delta G^0 = RT\ln K$$

where
$\Delta G^0$ = Gibbs free energy
K = equilibrium constant to equation 3, we obtain as an estimation of $K = 5.5 \times 10^{22}$. Thermodynamically this indicates feasibility of the reaction and that the product formed should be stable.

Accordingly, coated waveguides were prepared which incorporated $Fe_2(SO_4)_3$ as the active ingredient into the coating. These waveguides were then exposed to ammonia, which caused the expected color change, i.e. from off-white before exposure to violet after. The measured change was about 20% as opposed to waveguide rods which were not exposed to ammonium vapors. The colored product proved to be stable overnight, as hoped.

Waveguides were also prepared which incorporated ninhydrin(triketohydrindene hydrate) as the active ingredient in the coating. On exposure to ammonia, which caused the clear-colorless coating to turn blue, a change in transmittance of about 60% was found as opposed to waveguide rods which were not exposed to ammonia vapors. Both the ferric sulfate and ninhydrin can also be used to detect amines as well as ammonia. This is only another example of many different types of reagents that can be used to measure a component of interest. Sensitivity can be tailored by (1) selection of reagent, (2) the concentration of reagent used in the coating, (3) the coating thickness, and (4) the length of the waveguide.

EXAMPLE 3

A device of the invention was used to indicate the reaction of an antigen with an antibody on a quartz rod. The need for a simple test for disease and/or immunology detection using antibodies or antigens of all types and the broad operability of the present invention to fill this need is indicated by this example coupled with a recent article in Science News, by Dietrick, E. Thompson, "How a Nobel laureate solid-state physicist discovered a way of doing immunology by dunking, " Vol. 105, May 18, 1974, pages 324 and 5.

Polystyrene latex spheres about 1μ in diameter were treated with an excess of an antigen (human serum albumin) and the excess was then removed by repeated washings. Quartz rods silanized with diphenyl dimethoxy silane were coated with the corresponding antibody by incubating for 21 hours with a solution of anti human albumin at 1.0 mg/ml in 0.05 M bicarbonate buffer at pH 9.6, centrifuging and washing excess from the spheres. Uncoated portions of the rod surface can be filled by subsequent dipping of the rod in bovine serum albumin (BSA). The rods coated with specific and nonspecific antibody were exposed to a buffered solution containing the specific antigen (human albumin) coated polystyrene spheres.

The following results were obtained.

| Sample Concentration of Antigen Originally Applied to Polystyrene Latex Spheres | % Change in Axial Transmission of Rod Coated With Specific Antigen as Opposed to Rod Coated With Nonspecific Antigen |
|---|---|
| ≃1 mg/ml | −55.7% |
| ≃1 μg/ml | −17.6% |

EXAMPLE 4

Figure 5:
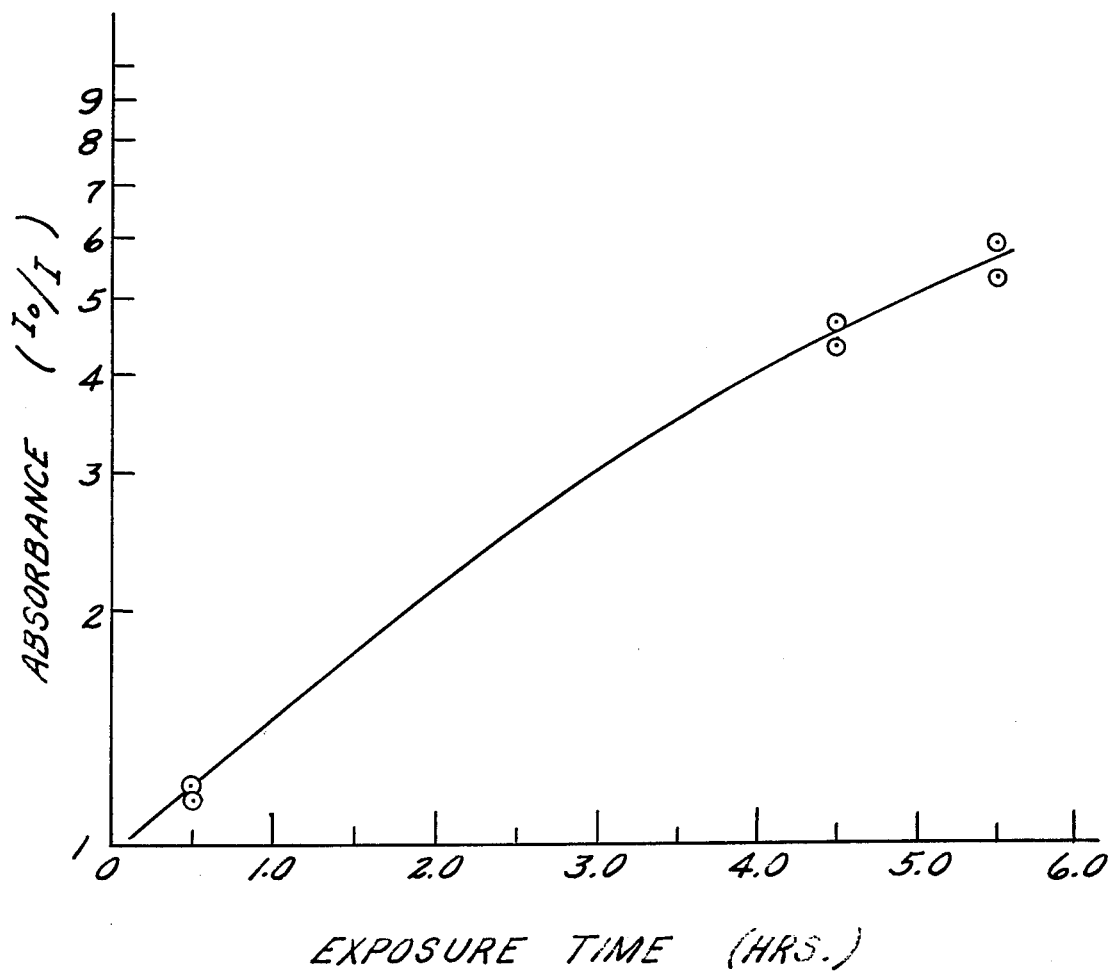

This example describes the detecting of hydrogen sulfide. Lead acetate reacts with $H_2S$ to produce a black precipitate of lead sulfide which scatters light. Using 1% lead acetate in polyvinyl acetate on the waveguide the results shown in FIG. 5 were obtained in the laboratory for a 6.7 ppm concentration of $H_2S$ in air.

The changes in the scattered axial transmission are measured by using an appropriate mask at the waveguide exit which masks mainly the direct light from the input aperture mask. These changes are due to scattering of the hollow cone of light launched into the waveguide because of the effect of the polystyrene spheres on the circumferential portion of the waveguides.

In the device and method of this example, light from a tungsten filament is directed via a lens system through a quartz rod to a photodiode detector, as in previous discussion on FIG. 3. When a coating is incorporated on the surface of the rod, the attenuation of light travelling through the rod varies. Thus, a measure of the amount of light transmitted through the entire rod and falling on the photodetector is indicative of the physical properties (refractive index, suspended solids, color, etc.) of the coating. Colored filters can be used to measure color changes in the coating.

There are significant differences in transmittance of different rods since each surface imperfection or scattering center has an effect. Therefore, each rod must be handled separately, or rods prepared or selected having substantially the same transmittance should be used.

Some illustrations of other materials which can be detected by a device of the invention are as follows:

1. Some experiments were carried out detecting $CO_2$. A polyvinyl alcohol coating containing a sodium carbonate/bicarbonate buffer and a methyl red indicator was applied to a waveguide. This coated waveguide was exposed to an atmosphere containing $CO_2$ and the coating changed from red to yellow which is measurably detected with the device. This reaction illustrative of the acid/base reaction is reversible (not permanent) and when the $CO_2$ atmosphere is removed from the waveguide the color changes back to red and thus the utility of the invention has been demonstrated both for permanent and reversible chemical reactions.

2. An illustration of a precipitate being formed is when an $SO_3$ containing atmosphere is contacted with a coated waveguide containing $BaCl_2$. Sufficient moisture is normally present in the air to form sulfuric acid from the $SO_3$ and the sulfuric acid reacts with $BaCl_2$ to form a precipitate $BaSO_4$, which has a coating on the waveguide will cause loss of light by scattering and so measurably reduce light transmission through the waveguide.

3. Phosgene can be detected using a rod coated with a reagent such as mixtures of p-dimethylaminobenzaldehyde and dimethylaniline or alternatively mixtures of p-nitrobenzylpyridine and N-benzylaniline. Other reagents useful for phosgene determination are:
   a. Methyl violet
   b. Methyl violet B
   c. Gentian violet
   d Rosaniline
   e. phenylhydrazine cinnamate and 1% copper sulfate
   f. p-dimethylaminobenzaldehyde and an aromatic amine
   g. diethylphthalate containing (4-nitrobenzyl)pyridine
   h. N-ethyl-N-2-hydroxylthylaniline and p-dimethylaminobenzaldehyde
   i. 4-(p-nitro-4,4-bis(dimethylamino)benzophenine
   j. 4,4'-bis(dimethylamino)benzophenone and N-phenyl-1-napthylamine Each reacts with phosgene to produce a colored compound.

4. Tolylene diisocyanate can be detected using a rod coated with a reagent such as p-dimethylaminobenzaldehyde mixed with acetic acid, or p-dimethylaminobenzaldehyde, sodium nitrite, boric acid and ethyl cellosolve mixed together.

5. Sulfur dioxide can be detected using a rod coated with mixtures of p-phenylenediamine and formaldehyde, mixtures of iodine and starch, or mixtures of potassium tetrachloromercurate, pararosaniline and formaldehyde. Other reagents which can be used for $O_2$ are:
   a. sodium tetrachloromercurate and pararosaniline
   b. zinc acetate, pyridine, and sodium nitroprusside
   c. zinc nitroprusside
   d. nickel hydroxide
   e. iodine and starch
   f. Meldola Blue
   g. Hydrine Blue R Each reacts with sulfide dioxide to form a colored adduct.

6. Carbon Monoxide — Reagents useful for the CO determination are:
   a. palladous chloride
   b. alkaline solution of the silver salt of p-sulfaminobenzoic acid
   c. tetrachloropalladate (II), iodate, and leucocrystal violet [4,4',4''-methylidynetris (N,N-dimethylaniline)] Each serves as a reagent for oxidation of CO, the accompanying reduction of metal ions providing the basis for a color change and/or precipitate formation.

7. Hydrogen Chloride (or Hydrochloric Acid Vapors)
   a. hydrogen ion (pH) indicators such as phenol red, methyl orange, methyl red, etc, in a procedure analogous to that for item (1), page 19.
   b. silver nitrate, which would provide both sensitivity and specificity through formation of the light scattering precipitate silver chloride.

8. $NO_x$ — Reagents useful for the $NO_x$ determination are:
   a. benzidine hydrochloride
   b. mixture of aniline and p-toludine
   c. 2,7-diaminofluorene, or 2,7-diaminofluorenehydrochloride
   d. 2,4-diamino-6-hydroxypyrimidine and $H_2SO_4$
   e. diethyldiphenyl urea
   f. $\beta$-dinaphthylamine and $H_2SO_4$
   g. diphenylamine Each results in formation of a colored or fluorescing adduct.

9. Ozone — Reagents useful for the ozone determination are:
   a. a mixture of $\alpha$-naphthylamine and tartaric acid
   b. o-phenylenediamine and HCl
   c. alcoholic solution of benzidine
   d. m-phenylenediamine hydrochloride
   e. p-phenylenediamine
   f. tetramethyl-p-phenylenediamine in acetic acid
   g. buffered potassium iodide Each utilizes the reaction with ozone to produce a colored product.

10. Hydrazine — Reagents useful for the hydrazine determination are:
    a. p-dimethylaminobenzaldehyde
    b. perinapthindan-2,3,4-trione hydrate Each produces a colored or fluorescing product.

The device, waveguides and method of this invention are especially useful in detecting toxic substances and/or atmospheric or water pollutants, for which a number of examples are given in this application. Some of the most significant atmospheric pollutants are combustion gases which consist essentially of CO, $CO_2$, $NO_x$, $SO_2$ and $SO_3$ in varying quantities depending on the materials and amounts thereof involved in combustion. Each of these combustion gases is dealt with in one of the specific numbered items listed above. A waveguide for each of these combustion gases can be included in a single waveguide holder to provide for the detection of all of these combustion gases at the same time.

Similar techniques to the above examples can be adapted to measurement of other components such as vinyl chloride, sulfuric acid, acrolein, maleic anhydride, formaldehyde, hydrogen fluoride, chlorine, fluorine, acetic acid, napthoquinone and phthalic anhydride.

Furthermore, techniques similar to the above examples can be adapted for functional group response of generic classes of compounds such as: alcohols, ketones, aldehydes, ethers, esters, halogen compounds, phenols, amines, and hydrocarbons.

In all applications of the device of the invention it is recognized that reagents and reaction conditions must be selected in accordance with the criteria of mutual compatibility, sensitivity, stability, and proportional response.

Many more illustrations could easily be provided by a person skilled in the art from chemistry texts or literature articles, such as, "Spot Tests In Inorganic Analysis":, Fritz Fergl, Elsevier Publishing Co., New York, (1958); or "Colorimetric Methods of Analysis, " F. D. Snell, C. T. Snell and C. A. Snell, D. Van Nostrand Co., Inc., New York, (1959).

A number of desirable features of the coated waveguide rods are:

1. They do not require batteries or other power sources since sample pumps, etc. are not required. However, it may be desirable to utilize a sample pump in conjunction with a coated waveguide for a future application.

2. They can be quantitatively measured for ammonia or hydrogen cyanide exposure or other materials by measuring the transmission when they are returned to the laboratory without any additional treatment.

3. The instrumentation for measurement is simple and inexpensive.

4. The coated waveguide rods can be sensitized to a variety of different compounds.

5. The classification of approaches made at the present time indicates a broad scope of application.

6. The sensitivity of the waveguide can be increased by increasing its length and this may be especially important in detecting minute quantities of environmental air pollutants such as ammonia, hydrogen cyanide, etc.

Although the invention has been described in terms of specified embodiments which are set forth in considerable detail, it should be understood that this is by way of illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed is:

1. A device for detecting a first material comprising
   a. an elongated waveguide having on a longitudinal peripheral surface of said waveguide a second material providing for multiple internal reflections of light through said material, which second material on contacting said first material selectively combines with said first material to measurably change the light transmitting capabilities of said waveguide,
   b. a light source positioned to transmit light into said waveguide, and
   c. means for measuring the light exiting from said waveguide.

2. A device of claim 1 wherein said waveguide is coated with a second material capable of detecting ammonia.

3. A device of claim 2 wherein said waveguide is coated with ferric sulfate dispersed in polyvinyl alcohol.

4. A device of claim 2 wherein said waveguide is coated with triketohydrindene hydrate dispersed in polyvinyl alcohol.

5. A device of claim 1 wherein said waveguide is coated with a second material capable of detecting hydrogen cyanide.

6. A device of claim 5 wherein said waveguide is coated with sodium picrate dispersed in polyvinyl alcohol.

7. A device of claim 1 wherein said waveguide is coated with a second material capable of detecting hydrogen sulfide.

8. A device of claim 7 wherein said waveguide is coated with lead acetate dispersed in polyvinyl acetate.

9. A device of claim 1 wherein said waveguide is coated with an antibody or an antigen.

10. A device of claim 1 wherein said waveguide is coated with a second material capable of detecting a combustion gas.

11. A device of claim 1 wherein said waveguide is coated with a second material capable of detecting a toxic substance.

12. An elongated waveguide having on a longitudinal peripheral surface of said waveguide a second material providing for multiple internal reflections of light through said material, which second material upon contacting a first material selectively combines said first material to measurably change the light transmitting capabilities of said waveguide.

13. A waveguide of claim 12 wherein said waveguide is coated with a second material capable of detecting ammonia.

14. A waveguide of claim 13 wherein said waveguide is coated with ferric sulfate dispersed in polyvinyl alcohol.

15. A waveguide of claim 13 wherein said waveguide is coated with triketohydrindene hydrate dispersed in polyvinyl alcohol.

16. A waveguide of claim 12 wherein said waveguide is coated with a second material capable of detecting hydrogen cyanide.

17. A waveguide of claim 16 wherein said waveguide is coated with sodium picrate dispersed in polyvinyl alcohol.

18. A waveguide of claim 12 wherein said waveguide is coated with a second material capable of detecting hydrogen sulfide.

19. A waveguide of claim 18 wherein said waveguide is coated with lead acetate dispersed in polyvinyl acetate.

20. A waveguide of claim 12 wherein said waveguide is coated with an antibody or an antigen.

21. A waveguide of claim 12 wherein said waveguide is coated with a second material capable of detecting a combustion gas.

22. A waveguide of claim 12 wherein said waveguide is coated with a second material capable of detecting a toxic substance.

23. A method for detecting a first material comprising the steps of
   a. exposing an elongated waveguide having on a longitudinal peripheral surface of said waveguide a second material providing for multiple internal reflections of light through said material, to an unknown material which may contain said first material, said second material upon being contacted by said first material selectively combines with said first material to measurably change the light transmitting capabilities of said waveguide;
   b. transmitting light through said waveguide after exposure in step (a); and,
   c. detecting the light transmitted in step (b) as a measure of said first material.

24. A method of claim 23 wherein said first material comprises ammonia.

25. A method of claim 24 wherein said waveguide is coated with ferric sulfate dispersed in polyvinyl alcohol.

26. A method of claim 24 wherein said waveguide is coated with triketohydrindene hydrate dispersed in polyvinyl alcohol.

27. A method of claim 23 wherein said first material comprises hydrogen cyanide.

28. A method of claim 27 wherein said waveguide is coated with sodium picrate dispersed in polyvinyl alcohol.

29. A method of claim 23 wherein said waveguide is coated with a second material capable of detecting hydrogen sulfide.

30. A method of claim 29 wherein said waveguide is coated with lead acetate dispersed in polyvinyl acetate.

31. A method of claim 23 wherein said waveguide is coated with an antibody and said first material comprises the antigen for said antibody.

32. A method of claim 23 wherein said waveguide is coated with an antigen and said first material comprises an antibody for said antigen.

33. A method of claim 23 wherein said waveguide is coated with a second material capable of detecting a combustion gas.

34. A method of claim 23 wherein said waveguide is coated with a second material capable of detecting a toxic substance.

* * * * *

UNITED STATES PATENT AND TRADEMARK OFFICE
CERTIFICATE OF CORRECTION

PATENT NO. : 4,050,895
DATED : September 27, 1977
INVENTOR(S) : EDGAR E. HARDY and DONALD J. DAVID It is certified that error appears in the above-identified patent and that said Letters Patent are hereby corrected as shown below:

Column 4, line 25, "$10^{31\ 11}$" should be changed to --- $10^{-11}$ --- and "$10^{31\ 3}$" should be changed to --- $10^{-3}$ ---.

Column 9, line 4, "has" should be changed to --- as ---;
line 39, "$O_2$" should be changed to --- $SO_2$ ---.

Signed and Sealed this

Fourth Day of April 1978

[SEAL]

Attest:

RUTH C. MASON
Attesting Officer

LUTRELLE F. PARKER
Acting Commissioner of Patents and Trademarks